(12) United States Patent
Khan et al.

(10) Patent No.: US 10,759,747 B2
(45) Date of Patent: Sep. 1, 2020

(54) ALKYLATION METHOD

(71) Applicants: GE HEALTHCARE LIMITED, Buckinghamshire (GB); KING'S COLLEGE LONDON, Greater London (GB)

(72) Inventors: Imtiaz Khan, Buckinghamshire (GB); Graeme McRobbie, Buckinghamshire (GB); Anna Kirjavainen, London (GB)

(73) Assignees: GE HEALTHCARE LIMITED, Birmingham (GB); KINGS COLLEGE LONDON, Greater London (GB)

( * ) Notice: Subject to any disclaimer, the term of this patent is extended or adjusted under 35 U.S.C. 154(b) by 0 days.

(21) Appl. No.: 16/097,571

(22) PCT Filed: May 2, 2017

(86) PCT No.: PCT/EP2017/060401
§ 371 (c)(1),
(2) Date: Oct. 29, 2018

(87) PCT Pub. No.: WO2017/186969
PCT Pub. Date: Nov. 2, 2017

(65) Prior Publication Data
US 2019/0161440 A1    May 30, 2019

(30) Foreign Application Priority Data
Apr. 29, 2016    (GB) .................................... 1607572.3

(51) Int. Cl.
*C07C 319/14*    (2006.01)

(52) U.S. Cl.
CPC ........ *C07C 319/14* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 2013/0060064 A1* | 3/2013 | Brathe | .................. C07B 59/001 |
| | | | 564/238 |
| 2014/0243555 A1* | 8/2014 | Nairne | ............... A61K 51/0406 |
| | | | 564/238 |

FOREIGN PATENT DOCUMENTS

| | | |
|---|---|---|
| CN | 103351317 A | 6/2005 |
| CN | 101253149 A | 8/2008 |
| CN | 102884043 A | 1/2013 |
| CN | 103857644 A | 6/2014 |
| CN | 103874672 A | 6/2014 |
| WO | WO 2004/007440 A1 | 1/2004 |
| WO | WO 2006/136846 A1 | 12/2006 |
| WO | WO 2011/141568 A1 | 11/2011 |
| WO | WO 2013/053940 A1 | 4/2013 |
| WO | WO 2013/053941 A1 | 4/2013 |

OTHER PUBLICATIONS

Robins, Edward G., et al., "Synthesis and in vitro evaluation of 18F-labelled S-fluroalkyl diarylguanidines: Novel high-affinity NMDA receptor antagonists for imaging with PET", Elsevier Ltd., Bioogranic & Medicinal Chemistry Letters, 20, (2010), pp. 1749-1751.

* cited by examiner

*Primary Examiner* — Sudhakar Katakam
*Assistant Examiner* — Jennifer C Sawyer
(74) *Attorney, Agent, or Firm* — Culhane Meadows, PLLC; Jeff B. Vockrodt

(57) ABSTRACT

The present invention relates to a method of radiochemical synthesis. Novel methods useful in the synthesis of a positron emission tomography (PET) tracer, and novel intermediates useful in said method are provided that have advantages over known methods.

34 Claims, 5 Drawing Sheets

ALKYLATION METHOD

CROSS-REFERENCE TO RELATED APPLICATIONS

This application is a 35 U.S.C. 371 National Phase of PCT Application No. PCT/EP2017/060401, filed on May 2, 2017, which claims priority to GB Application No. 1607572.3 filed Apr. 29, 2016, the disclosures of each of which are hereby incorporated by reference in their entirety.

The work leading to this invention has received funding from the People Programme (Marie Curie Actions) of the European Union's Seventh Framework Programme (FP7/2007-2013) under REA grant agreement Number 316882.

TECHNICAL FIELD OF THE INVENTION

The present invention resides in the field of chemical synthesis. More specifically, the present invention relates to novel methods useful in the synthesis of a positron emission tomography (PET) tracer, and novel intermediates useful in said method.

DESCRIPTION OF RELATED ART

WO 2004/007440 and WO 2006/136846 describe radiolabelled guanidine derivatives and their use for imaging central nervous system (CNS) receptors and teach synthesis of these radiolabelled derivatives from precursor compounds. For example, WO 2006/136846 teaches a compound of Formula (A):

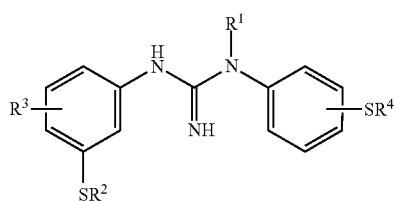

or a salt or solvate thereof, wherein:
R$^1$ is hydrogen or C$_{1-4}$ alkyl,
R$^2$ and R$^4$ are each independently selected from C$_{1-4}$ alkyl, [$^{11}$C]—C$_{1-4}$alkyl, and [$^{18}$F]—C$_{1-4}$ fluoroalkyl provided that at least one of R$^2$ and R$^4$ is [$^{11}$C]—C$_{1-4}$alkyl or [$^{18}$F]—C$_{1-4}$ fluoroalkyl, and,
R$^3$ is halo.

WO 2006/136846 teaches that the above compound of Formula (A) is synthesised by reaction of a suitable source of $^{11}$C or $^{18}$F with a precursor compound of Formula (B):

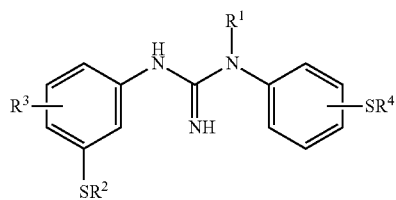

wherein one of R$^2$ or R$^4$ is hydrogen, and the other is hydrogen, C$_{1-4}$ alkyl, or a thiol protecting group such as benzyl; R$^1$ is hydrogen or C$_{1-4}$ alkyl, and R$^3$ is halo.

WO 2006/136846 also teaches that the method to obtain the precursor compound of Formula (B) above wherein R$^2$ is hydrogen is based on that disclosed by Hu et al (J. Med. Chem. 1997; 40(26): 4281-9), wherein a compound of Formula (C):

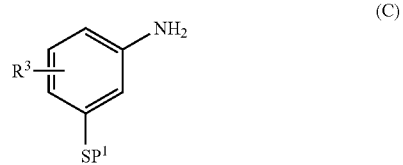

or a salt or solvate thereof, wherein R$^3$ is halo and P$^1$ is a thiol protecting group; is reacted with a compound of Formula (D):

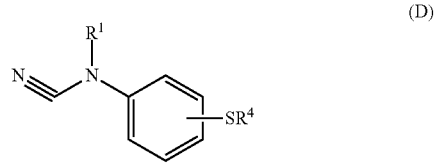

wherein R$^1$ is hydrogen or C$_{1-4}$ alkyl and R$^4$ is as defined for the desired compound of Formula (B).

This method has also been recently reported by Robins et al (2010 Bioorg Med Chem Lett; 20: 1749-51) as a successful way to obtain the following $^{18}$F-labelled S-fluoroalkyl diarylguanidines:

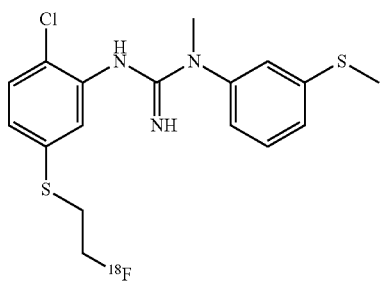

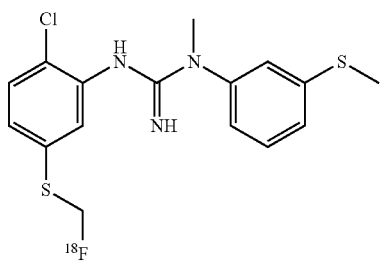

WO 2011/141568 developed the above-described methods further by using a dimeric precursor compound of the following structure:

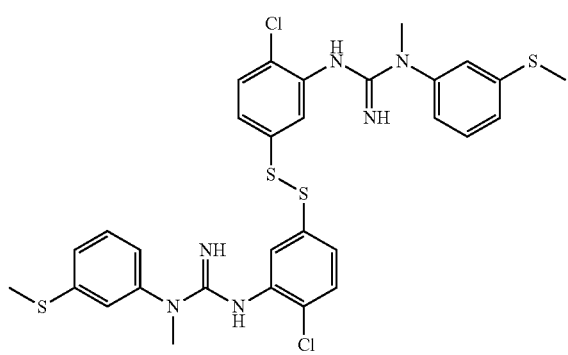

The above disulfide precursor is reduced to the thiol prior to reaction with a radiolabelled alkylating agent in order to obtain the above-described radiolabelled guanidine derivatives.

There is scope to improve the synthesis of radiolabelled guanidine derivatives, in particular with a view to automation.

SUMMARY OF THE INVENTION

In one aspect the present invention relates to a method to obtain a compound of Formula I:

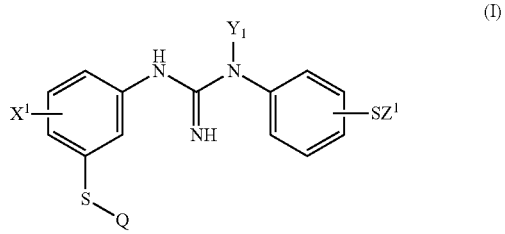

wherein:
X$^1$ is an X group selected from C$_{1-4}$ alkyl or halo;
Y$^1$ is a Y group selected from hydrogen or C$_{1-4}$ alkyl;
Z$^1$ is a Z group which is C$_{1-4}$ alkyl; and,
Q is [$^{11}$C]C$_{1-4}$ alkyl- or [$^{18}$F]—C$_{1-4}$ fluoroalkyl-,
wherein said method comprises:
(i) reducing a compound of Formula II:

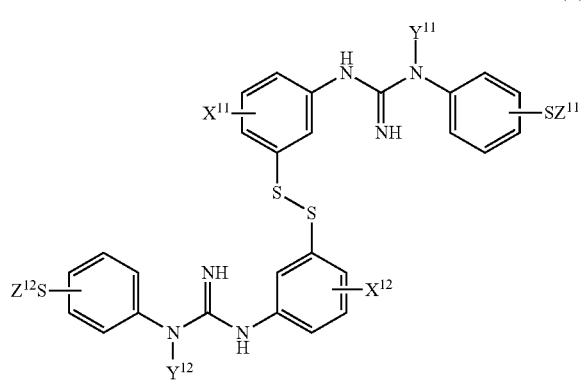

wherein:
X$^{11}$ and X$^{12}$ are the same and are both an X group as defined for X$^1$,
Y$^{11}$ and Y$^{12}$ are the same and are both a Y group as defined for Y$^1$, and,
Z$^{11}$ and Z$^{12}$ are the same and are both a Z group as defined for Z$^1$, and,
(ii) adding a base to the product of step (i) and reacting with either [$^{11}$C]C$_{1-4}$ alkyl-LG$^1$ or [$^{18}$F]—C$_{1-4}$ fluoroalkyl-LG$^2$, wherein LG$^1$ and LG$^2$ are independently halo, or the group —O—SO$_2$—R$^1$ wherein R$^1$ represents an optionally-substituted C$_{6-10}$ aryl, an optionally-substituted C$_{1-4}$ alkyl, or C$_{1-4}$ fluoroalkyl;
wherein the molar ratio of added base:thiol in step (ii) is in the range of about 0.2-1.0.

The method of the present invention is particularly suitable for automation. Furthermore, using the method of the invention provides the compound of Formula I with improved yields and lower impurity levels compared to previous methods.

DETAILED DESCRIPTION OF THE PREFERRED EMBODIMENTS

Figure 1:
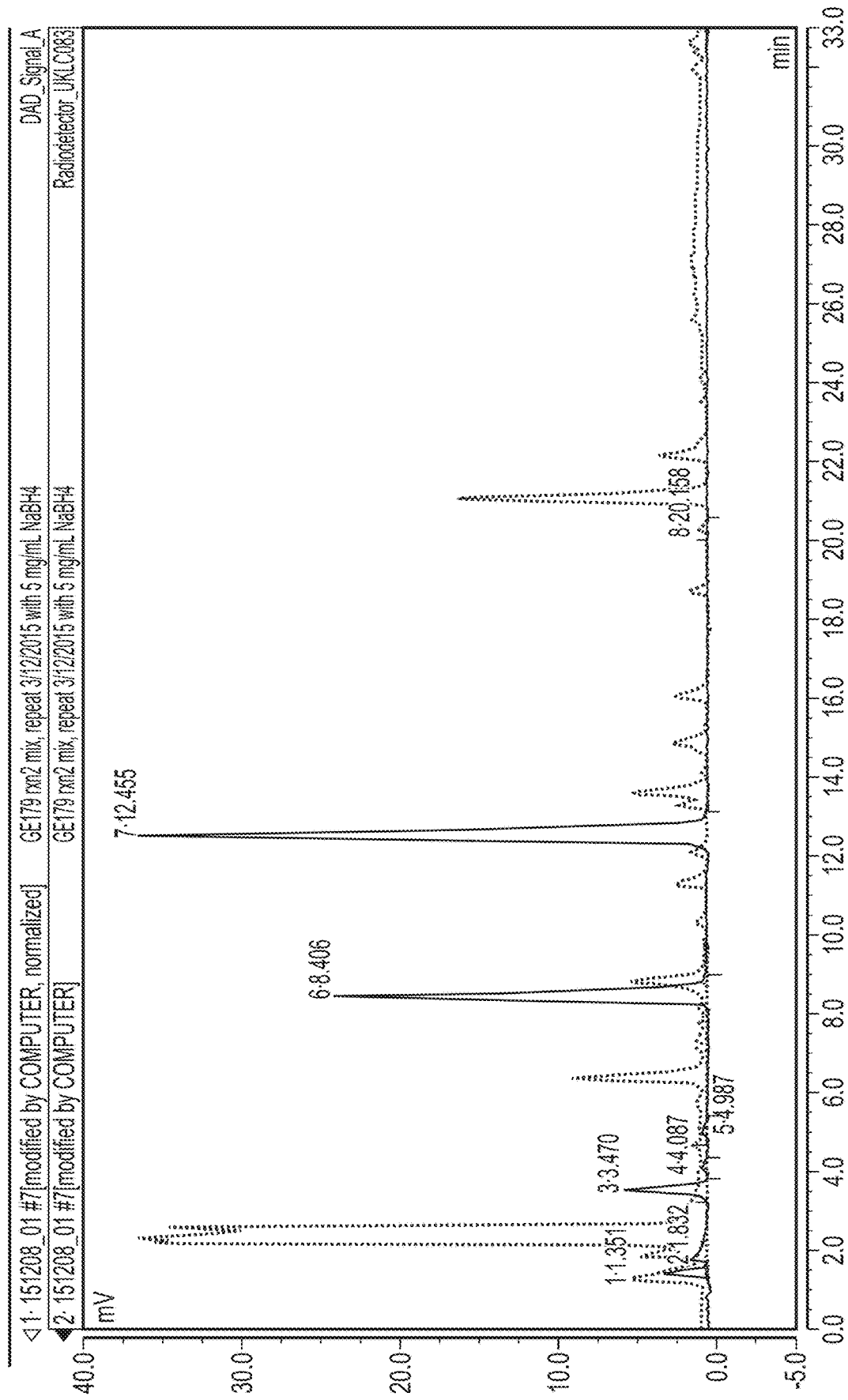
FIG. 1 shows a trace of crude [$^{18}$F]GE-179 when using only ethanolic NaBH$_4$ with 3.5% water to increase pH of the reaction solution.

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "alkyl", alone or in combination, means a straight-chain or branched-chain alkyl radical having the general formula C$_n$H$_{2n+1}$. Examples of such radicals include methyl, ethyl, and isopropyl.

"Fluoroalkyl" is an alkyl group as defined above substituted with one or more fluorine atoms. In one embodiment said one or more fluorine atoms is suitably an $^{18}$F atom. In one embodiment of the invention the fluorine replaces a hydrogen at the terminal end of the radical, i.e. -alkylenefluoro.

The term "halogen" or "halo-" means a substituent selected from fluorine, chlorine, bromine or iodine.

The term "base" is used herein in the chemical sense of being a proton acceptor.

The step of the inventive method of reacting with the alkylhalide is carried out in a suitable solvent. Suitable solvents include N,N-dimethylformamide (DMF), acetone, dichloromethane, chloroform, dimethylsulphoxide, methanol, ethanol, propanol, isopropanol, tetrahydrofuran or acetonitrile and in the presence of a base. In one embodiment the suitable solvent for this step is ethanol. In certain embodiments the base is an inorganic base such as potassium carbonate, potassium hydroxide, or sodium hydride, or an organic base such as a trialkylamine, for example triethylamine, diisopropylethylamine, or dimethylaminopyridine. In one embodiment the base is potassium carbonate. In one embodiment where Q in Formula I is [$^{18}$F]—C$_{1-4}$ fluoroalkyl- the base is the same reagent that is used to elute $^{18}$F-fluoride from the QMA column in the process for preparation of $^{18}$F-fluoride. The specific molar ratio of base:thiol was found by the present inventors to be particularly advantageous in obtaining a crude radiolabelled product in high yields and also relatively free of impurities as compared with the prior process.

[$^{11}$C]C$_{1-4}$ alkyl-LG$^1$ can be prepared using methods well-known in the art of radiochemistry. For example, [$^{11}$C] methyl iodide can be prepared by reduction of [$^{11}$C]carbon dioxide with lithium aluminium hydride followed by reaction with hydroiodic acid. [$^{11}$C]Carbon dioxide is usually produced by the 41 N($\rho,\alpha$)$^{11}$C reaction from nitrogen gas containing trace amounts of oxygen. [$^{11}$C]Methyl triflate can be prepared from [$^{11}$C]methyl iodide, or by gas phase reaction of [$^{11}$C]methyl bromide prepared from [$^{11}$C]methane. All these methods are described in more detail in "Aspects on the Synthesis of $^{11}$C-Labelled Compounds", Chapter 3 of Handbook of Radiopharmaceuticals (2003 Welch & Redvanly eds. pp 141-194). A preferred [$^{11}$C]C$_{1-4}$ alkyl-LG$^1$ is selected from [$^{11}$C]methyl-LG$^1$ or [$^{11}$C]ethyl-LG$^1$, and LG$^1$ is preferably iodo.

[$^{18}$F]—C$_{1-4}$ fluoroalkyl-LG$^2$ can be prepared by radiolabelling alkyldihalides or sulfonates using [$^{18}$F]fluoride. [$^{18}$F] Fluoride is typically obtained as an aqueous solution which is a product of the irradiation of an [$^{18}$O]-water target. It has been widespread practice to carry out various steps in order to convert [$^{18}$F]Fluoride into a reactive nucleophilic reagent, such that it is suitable for use in nucleophilic radiolabelling reactions. These steps include the elimination of water from [$^{18}$F]-fluoride ion and the provision of a suitable counterion (Handbook of Radiopharmaceuticals 2003 Welch & Redvanly eds. ch. 6 pp 195-227). Suitable counterions include large but soft metal ions such as rubidium or caesium, potassium complexed with a cryptand such as Kryptofix™, or tetraalkylammonium salts. A preferred [$^{18}$F]—C$_{1-4}$ fluoroalkyl-LG$^2$ is [$^{18}$F]-fluoroethyl-LG$^2$ wherein LG$^2$ is preferably a sulfonate, most preferably tosylate.

The dimer precursor can be obtained by the methods described in WO 2011/141568. In summary, a cyanamide starting material is prepared according to the method described by Hu et al (1997 J Med Chem; 40: 4281-4289), by reaction of cyanogen bromide with the primary amine in diethyl ether, or by alkylation of an arylcyanamide with sodium hydride or alkyl halide in tetrahydrofuran. The nitrobenzenesulfonyl chloride starting material is commercially available. The first step is reduction of the nitrobenzenesulfonyl chloride starting material to form an aminobenzenethiol intermediate. The disulfide is obtained in the method of the invention by iodine oxidation of the aminobenzenethiol intermediate.

In one embodiment of the method of the invention said compound of Formula II is a compound of Formula IIa:

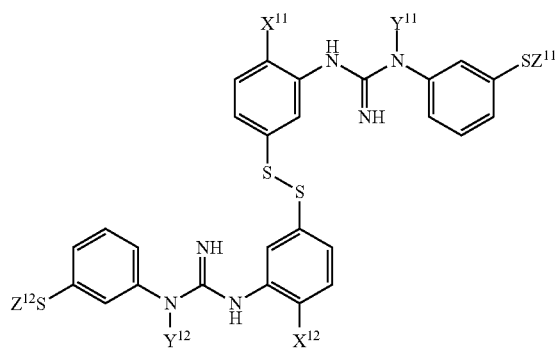

(IIa)

wherein:

X$^{11}$ and X$^{12}$ are the same and are both an X group as defined herein;

Y$^{11}$ and Y$^{12}$ are the same and are both a Y group as defined herein; and, Z$^{11}$ and Z$^{12}$ are the same and are both a Z group as defined herein.

In one embodiment of the method of the invention said X group is halo.

In one embodiment of the method of the invention said Y group is 01-4 alkyl.

In one embodiment of the method of the invention said Z group is methyl.

In one embodiment of the method of the invention said X group is chloro, said Y group is methyl and said Z group is methyl.

In one embodiment of the method of the invention said reducing step (i) is effected using a reducing agent selected from sodium borohydride (NaBH$_4$), free phosphines, 1,8-Diazabicyclo[5.4.0]undec-7-ene (DBU), zinc in hydrochloric acid, zinc in acetic acid, magnesium in hydrochloric acid, sodium hydrogentelluride (NaTeH) in ethanol, lithium aluminium hydride (LAIN in tetrahydrofuran, indium in ammonium chloride, and sodium hydride (NaH), or a solid bound reducing agent such as triphenyl phosphone or phosphine.

In one embodiment of the method of the invention said reducing step (i) is effected using NaBH$_4$.

In one embodiment of the method of the invention said reacting step (ii) the thiol product is reacted with [$^{18}$F]—C$_{1-4}$ fluoroalkyl-LG$^2$.

In one embodiment of the method of the invention said compound of Formula I is:

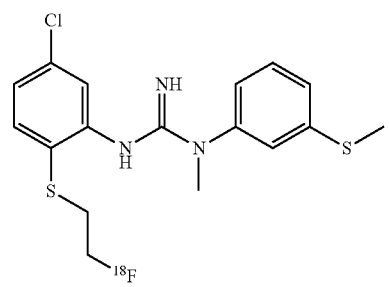 [SMILES: CSc1cccc(N(C)C(=N)Nc2cc(Cl)ccc2SCC[18F])c1]

The above compound of Formula I is also referred to herein as [$^{18}$F]-GE179, i.e. N-(2-Chloro-5-(2-[$^{18}$F]-fluoroethylthio))-phenyl-N'-(3-methylthio)-phenyl-N'-methyl-guanidine.

In one embodiment of the method of the invention said compound of Formula II is:

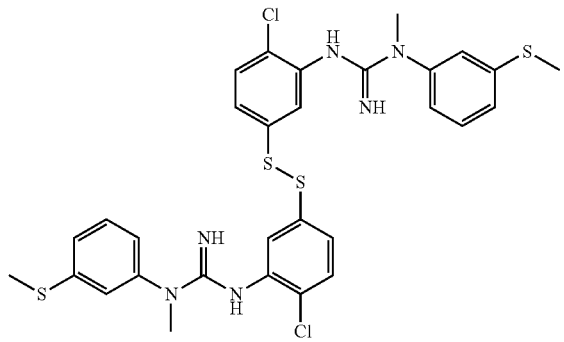

In one embodiment of the method of the invention said reducing step (i) and said reacting step (ii) are carried out in the same vessel.

In one embodiment of the method of the invention said reacting step is carried out in an ethanolic solution.

In one embodiment of the method of the invention said ratio of base:thiol is about 0.2-1.0.

In one embodiment of the method of the invention said ratio of base:thiol is about 0.2-0.5.

In one embodiment of the method of the invention said ratio of base:thiol is about 0.5-1.0.

In one embodiment of the method of the invention said ratio of base:thiol is about 0.5-0.75.

In one embodiment of the method of the invention said ratio of base:thiol is about 0.7-0.75.

In one embodiment of the method of the invention said reaction step (ii) is carried out for about 5-15 minutes.

In one embodiment of the method of the invention said reaction step (ii) is carried out for about 5-10 minutes.

In one embodiment of the method of the invention said reaction step (ii) is carried out for about 4.5-5.5 minutes.

In one embodiment of the method of the invention said reaction step (ii) is carried out for about 5.5 minutes.

In one embodiment of the method of the invention said reacting step (ii) comprises about 0.02-0.04 mmol thiol.

In one embodiment of the method of the invention said reacting step (ii) comprises about 0.02-0.035 mmol thiol.

In one embodiment of the method of the invention said reacting step (ii) comprises about 0.03-0.035 mmol thiol.

In one embodiment of the method of the invention said reacting step (ii) comprises about 0.005-0.025 mmol base.

In one embodiment of the method of the invention said reacting step (ii) comprises about 0.01-0.025 mmol base.

In one embodiment of the method of the invention said reacting step (ii) comprises about 0.02-0.025 mmol base.

In one embodiment of the method of the invention said reacting step (ii) is carried out at a temperature between about 80-120° C.

In one embodiment of the method of the invention said reacting step (ii) is carried out at a temperature between about 100-120° C.

In one embodiment of the method of the invention said reacting step (ii) is carried out at a temperature between about 105-110° C.

In one embodiment of the method of the invention said reacting step (ii) is carried out at a temperature of about 110° C.

In one embodiment of the method of the invention said compound of Formula I is:

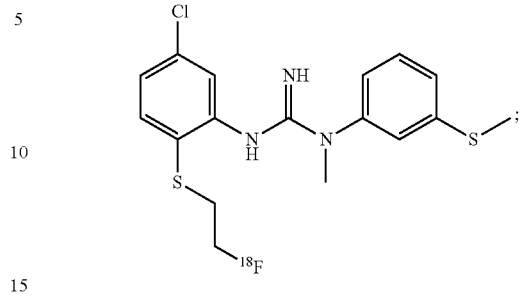

said compound of Formula II is:

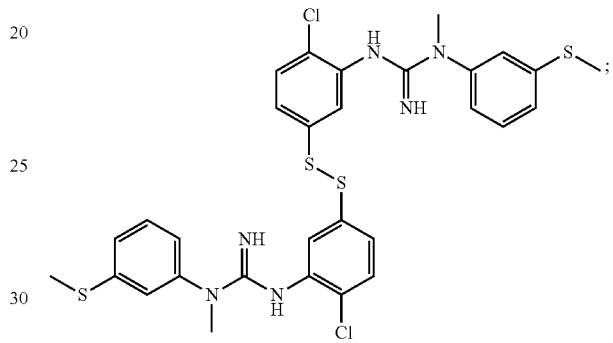

said ratio of base:thiol is about 0.2-0.75; and, said reacting step (ii) is carried out for about 5.5 minutes at about 110° C.

In one embodiment the method of the invention further comprises step (iii) purifying the reaction mixture obtained in step (ii) using solid phase extraction (SPE).

In one embodiment of the method of the invention said SPE is carried out using one or more reverse phase SPE cartridges.

In one embodiment of the method of the invention said SPE is carried out using one or more tC18 SPE cartridges.

In one embodiment of the method of the invention said SPE is carried out using two tC18 SPE cartridges.

In one embodiment of the method of the invention said SPE is carried out using two environmental tC18 SPE cartridges.

In one embodiment of the method of the invention said chemical impurities are removed from said tC18 SPE cartridges using a basic aqueous acetonitrile solution and said purified compound of Formula I is eluted from said tC18 SPE cartridges with an ethanol solution. In one embodiment said ethanol solution is an acidified ethanol solution.

In one embodiment of the method of the invention said method is automated. PET tracers, and in particular [$^{18}$F]-tracers are now often conveniently prepared on an automated radiosynthesis apparatus. There are several commercially-available examples of such apparatus, including Tracerlab™ and Fastlab™ (both from GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

BRIEF DESCRIPTION OF THE EXAMPLES

Example 1 describes the synthesis of [$^{18}$F]fluoroethyltosylate.

Example 2 describes the synthesis of 1,1'-(5,5'-disulfanediylbis(2-chloro-5,1-phenylene))bis(3-methyl-3-(3-(methylthio)phenyl)guanidine).

Example 3 describes the alkylation of the dimeric precursor with [$^{18}$F]fluoroethyltosylate on FASTlab™.

Example 4 describes an SPE process used to purify

List of Acronyms and Abbreviations Used in the Examples
chem. imp. chemical impurities
DCM dichloromethane
DMSO dimethylsulfoxide
eq equivalent(s)
EtOH ethanol
Et(OTs)$_2$ ethyl ditosylate
FEtOTs flouroethyl tosylate
HPLC high performance liquid chromatography
MeCN acetonitrile
min minute(s)
OTs tosylate
QMA quaternary methyl ammonium
RCY radiochemical yield
RV reaction vessel
SPE solid phase extraction
temp. temperature

EXAMPLES

Example 1: Synthesis of [$^{18}$F]fluoroethyltosylate

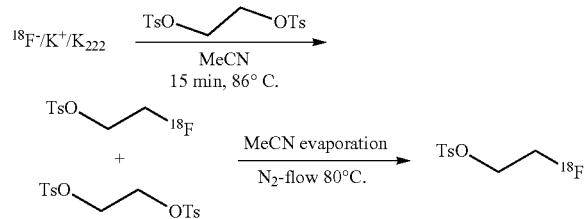

Aqueous [$^{18}$F]fluoride solution (~4.5 mL, 200 MBq-1.5 GBq) in $^{18}$O enriched water was delivered to the synthesizer through a Teflon line. The activity was trapped on a QMA SPE cartridge and [$^{18}$O]H$_2$O captured in a separate vial allowing for later recovery. The radioactivity was eluted into the reaction vessel with an aqueous ethanol solution containing potassium carbonate (K$_2$CO$_3$) (0.7-3 mg, 5.1-21.7 μmol) and 4,7,13,16,21,24-Hexaoxa-1,10-diazabicyclo [8.8.8]hexacosane (K$_{222}$) (3.7-12 mg, 9.8-31.9 μmol). The volume of H$_2$O and EtOH used to dissolve carbonate and K222 and elute QMA cartridge were varied (either 1 mL solution containing 15 mg/mL K$_2$CO$_3$ in H$_2$O (0.33 mL) and 15 mg/mL K$_{222}$ in EtOH (1.32 mL); or 90 μL solution containing 14.2. mg K$_2$CO$_3$/0.2 mL H$_2$O and 79 mg K$_{222}$/1.3 mL EtOH; or 200 μL H$_2$O and 1.3 mL EtOH with 14.2 mg K$_2$CO$_3$ and 79 mg K$_{222}$). To ensure the elution of [$^{18}$F]fluoride from QMA cartridge to the reaction vessel the highly concentrated base/K$_{222}$ solution (90 μL, 9 μL H$_2$O and 61 μL EtOH) was diluted with 200 μL water.

The evaporation step was an azeotropic method where eluent (around 90 μL) was drawn into syringe 1 followed by water (around 120 μL) and then followed by acetonitrile (around 400 μL). This eluted trapped $^{18}$F from the QMA cartridge into the reaction vessel, which was dried to obtain the anhydrous [$^{18}$F]F$^-$/K$_{222}$/K$^+$ complex using the following conditions:

a) 100° C./1 min b) 120° C./10 min c) 105° C./1.2 min

The total drying time was around 12 mins. At around 5.7 mins into the drying step, 1×500 ul of MeCN was added to the RV to azeotropically remove any remaining water. The drying continued for another 6.3 mins.

After drying $^{18}$F-fluoride, ethylene ditosylate (Et(OTs)$_2$, 2.7-18.5 mg, 7.4-19.2 μmol) in anhydrous MeCN or DMSO was added into the reactor. The labelling reaction was conducted at 86-105° C. for 2.5-15 min.

The table below shows the reaction conditions of [$^{18}$F] FEtOTs radiolabelling and achieved radiochemical yields (RCY).

| Reaction solvent | K$_2$CO$_3$ [umol] | K$_{222}$ [umol] | Et(OTs)$_2$ [umol] | Reaction time [min] | Reaction temp. [° C.] | RCY [%] |
|---|---|---|---|---|---|---|
| DMSO (1.3 mL) | 5.1 | 9.8 | 11.9 | 10 | 86 | 57* |
| MeCN (1.3 mL) | 21.7 | 31.9 | 19.2 | 10 | 86 | 47 |
| MeCN (1.3 mL) | 5.1 | 9.8 | 15.1 | 10 | 86 | 69 |
| MeCN (1.3 mL) | 5.1 | 9.8 | 8.1 | 15 | 86 | 80* |
| MeCN (2.1 mL) | 6.2 | 12.7 | 9.5 | 2.5 | 105 | 80 |

*Non-isolated yield.

3.5 mg (9.5 μmol) Et(OTs)$_2$ was enough to achieve high [$^{18}$F]FEtOTs RCYs. MeCN was the best option as a reaction solvent. With MeCN high radiochemical yields of [$^{18}$F] FEtOTs were obtained and MeCN is easier to remove from reaction mixture by evaporation prior to the alkylation step.

The reaction solvent was changed from MeCN to EtOH by evaporating MeCN away under N$_2$-flow at either 80° C. or 105° C. and dissolving the residual with EtOH.

Example 2: Synthesis of 1,1'-(5,5'-disulfanediylbis(2-chloro-5,1-phenylene))bis(3-methyl-3-(3-(methylthio)phenyl)guanidine)

Synthesis of 5,5'-disulfanediylbis(2-chlorobenzenaminium) chloride

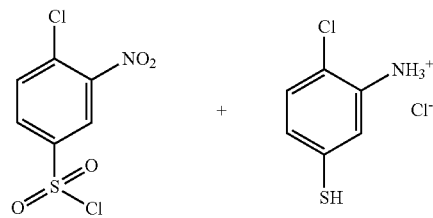

Synthesis of 1,1'-(5,5'-disulfanediylbis(2-chloro-5,1-phenylene))bis(3-methyl-3-(3-(methylthio)phenyl)guanidine)

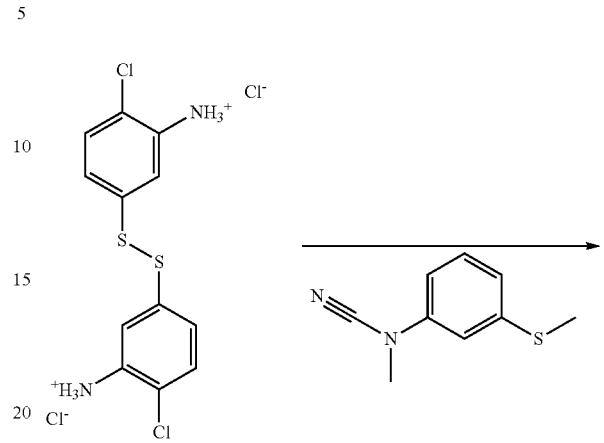

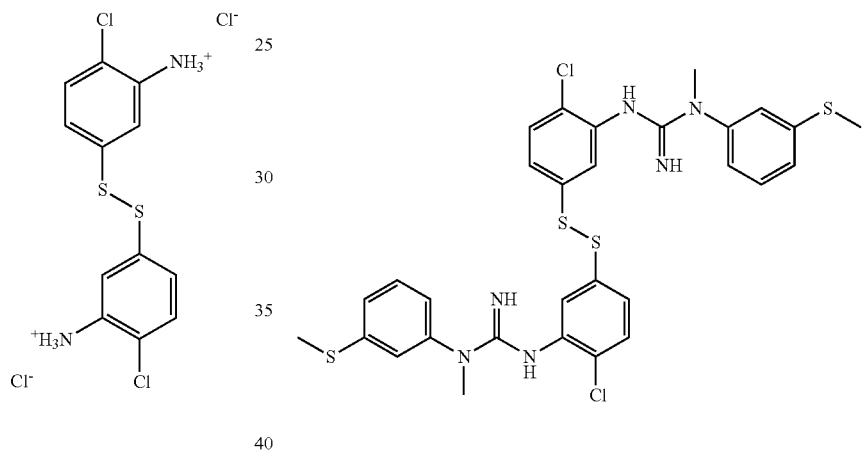

Tin(II) chloride (33.32 g, 175.74 mmol) was dissolved in 30% hydrochloric acid (99.7 mL) and 4-chloro-3-nitrobenzene-1-sulfonyl chloride (5.00 g, 19.553 mmol) was added before submerging the flask in a 125° C. preheated oil bath. After 3 hours all solid material had dissolved and the reaction mixture was allowed to cool to RT, which caused spontaneous crystallization.

The crystals (contaminated with Tin) were filtered off, dissolved in water (250 mL) and portions of iodine solution (50 mg/mL) were added until HPLC analysis confirmed that all the 2-chloro-5-mercaptobenzenaminium chloride had been converted to 5,5'-disulfanediylbis(2-chlorobenzenaminium) chloride. The solution was filtered, and water (400 mL) was added to the filtrate, followed by stirring and neutralization using NaOH solution (~1 mL, 10%). The solution was extracted with diethyl ether (4×150 mL), dried with magnesium sulphate (anhydrous) and filtered. To the ether solution was added HCl (dry, 1M in diethyl ether, 10 mL), the solution was filtered and the filtrate was dried under vacuum to give 5,5'-disulfanediylbis(2-chlorobenzenaminium) chloride as an off-white powder (21.47 g, 63%).

$^1$H NMR (400 MHz, CDCl$_3$): δ 7.154 (d, J=8.3 Hz, 2H), δ 6.865 (d, J=2.2 Hz, 2H), δ 6.783 (dd, J$_1$=2.2 Hz, J$_2$=8.3 Hz, 2H), δ 4.080 (broad s, 4H)

A mixture of 5,5'-disulfanediylbis(2-chlorobenzenaminium) chloride (1.0 g, 2.6 mmol) and N-methyl-N-(3-(methylthio)phenyl)cyanamide (1.83 g, 10.3 mmol) was heated to 130° C. This thick slow-stirring melt was left for 17 h (HPLC yield after 1 hour~80%), then allowed to cool to RT. The solid was dissolved in DCM (25 mL), extracted with water (3×200 mL) and the combined aqueous phases back-extracted with DCM (50 mL). The aqueous phase was neutralised with NaHCO$_3$ and extracted with diethyl ether (3×150 mL). The combined organic phases were dried with magnesium sulphate (~5 g), filtered and concentrated to dryness under reduced pressure to give 1,1'-(5,5'-disulfanediylbis(2-chloro-5,1-phenylene))bis(3-methyl-3-(3-(methylthio)phenyl)guanidine) (1.16 g, 1.7 mmol, 67%, HPLC purity 94.8%) as off-white powder.

$^1$H NMR (400 MHz, CDCl$_3$): δ 7.300 (t, J=7.9 Hz, 2H), δ 7.298 (d, J=8.3 Hz, 2H), δ 7.175 (t, J=1.9 Hz, 2H), δ 7.122 (ddd, J$_1$=1.0, J$_2$=1.8 Hz, J$_3$=7.9 Hz, 2H), δ 7.108 (d, J=2.3 Hz, 2H), δ 7.054 (ddd, J$_1$=1.0, J$_2$=2.2 Hz, J$_3$=7.9 Hz, 2H), δ 7.049 (dd, J$_1$=2.3, J$_2$=8.3 Hz, 2H), δ 3.893 (broad s, 4H), δ 3.338 (s, 6H), δ 2.494 (s, 6H).

Example 3: Alkylation of Dimeric Precursor with [¹⁸F]fluoroethyltosylate on FASTlab™

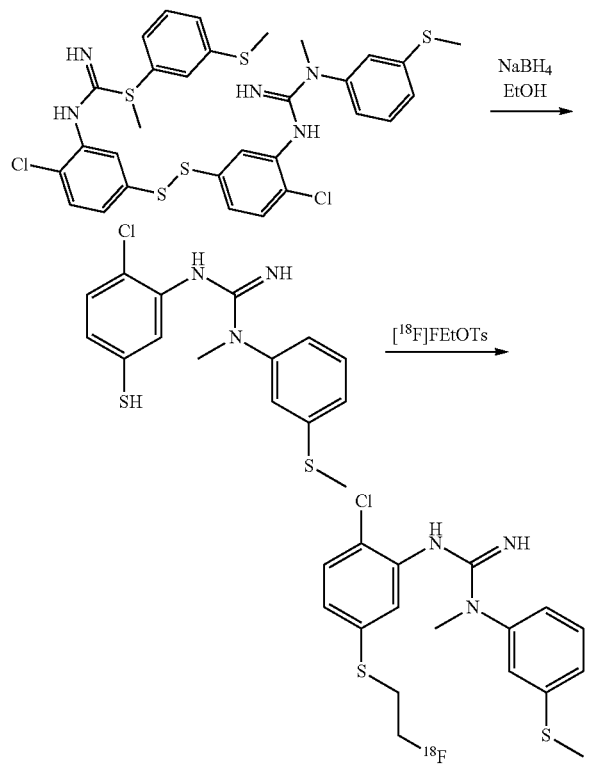

The dimer precursor was reduced as a monomeric thiol with sodium borohydride (NaBH₄). Different ways to mix reducing agent and dimer precursor were studied. Different amounts of NaBH₄ were tested (1-10 mg, 26-260 umol, 1.6-16 eq to molar amount of dimer). The lowest amount of NaBH₄ studied was 26 μmol, 1.6 eq and it was observed to be enough to reduce dimer precursor effectively and rapidly to thiol.

The reduction of the dimer precursor to free thiol was performed in the FASTlab reagent vial in parallel with the [¹⁸F]fluoroethyl tosylate labelling reaction. Over 95% reduction was achieved in 5 minutes using ethanolic solution of NaBH₄ at room temperature.

FIG. 1 shows a trace of crude [¹⁸F]GE-179 when using only ethanolic NaBH₄ with 3.5% water to increase pH of the reaction solution. Non-isolated radiochemical yield of [¹⁸F]GE-179 was 53%. The yield was calculated from the crude trace and isolated crude activity.

Optimisation of alkylation conditions using chemometrics:
  Studied parameters: Amount of precursor, time and temperature
  Optimised for level of chemical impurities and radiochemical yield
  12 experiments in total as detailed in the table below:

| Exp. | Time (min) | Temp. (° C.) | Dimer (mg) | Conversion (%) | Chem. Imp. (peak area) |
|---|---|---|---|---|---|
| 1 | 2 | 80 | 4 | 20 | 32 |
| 2 | 15 | 80 | 4 | 44 | 138 |
| 3 | 2 | 120 | 4 | 59 | 34 |
| 4 | 15 | 120 | 4 | 45 | 99 |
| 5 | 2 | 80 | 11 | 50 | 13 |
| 6 | 15 | 80 | 11 | 93 | 16 |
| 7 | 1 | 120 | 11 | 84 | 17 |
| 8 | 15 | 120 | 11 | 88 | 17 |
| 9 | 8.5 | 100 | 7.5 | 78 | 30 |
| 10 | 8.5 | 100 | 7.5 | 92 | 30 |
| 11 | 8.5 | 100 | 7.5 | 89 | 49 |
| 12 | 5.4 | 110 | 14 | 95 | 6 |

The table below summarises the best reaction conditions for highest RCY and lowest amount of impurities:

|  | Best conditions for high RCY | Best conditions for lowest chemical impurities | Chosen reaction conditions |
|---|---|---|---|
| Dimer (mg) | 11 | >9.8 | 10 |
| Temp. (° C.) | 110 | n/a | 110 |
| Time (min) | 11.7 | <5.2 | 5.5 |

Analytical method for [¹⁸F]GE-179:

| 0-1 mins | 40%(B) |
| 1-25 mins | 40-95%(B) |
| 25-30 mins | 95%(B) |
| 30-31 mins | 95-40%(B) |
| 31-33 mins | 40%(B) |

Column
Luna C18(2) column, 5 u, 150×4.6 mm
Mobile Phase
Mobile phase A (pump A): Acetonitrile (pump B)

| Loop Size | 20 μL |
| Pump speed | 1 mL/min |
| UV Sensitivity | 0.2 AUF |
| Wavelength | 254 nm |

Figure 2:
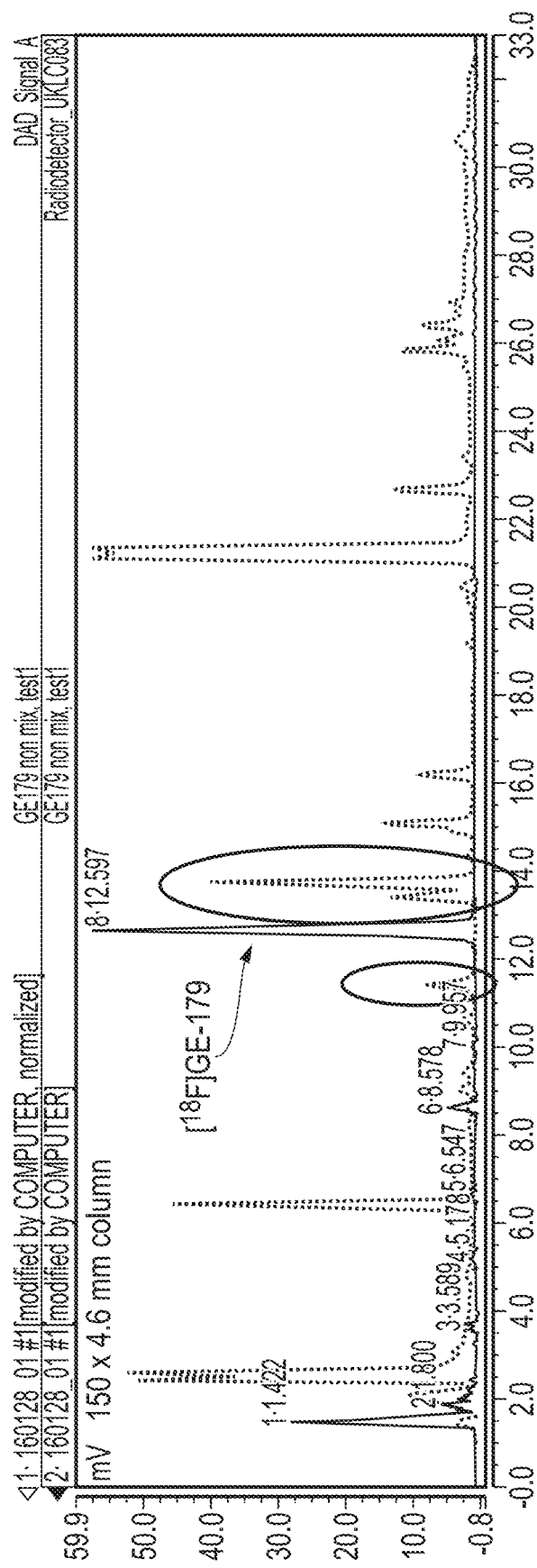
FIG. 2 is the HPLC trace from reaction crude of [$^{18}$F]GE-179 before and after optimization.
Figure 2:
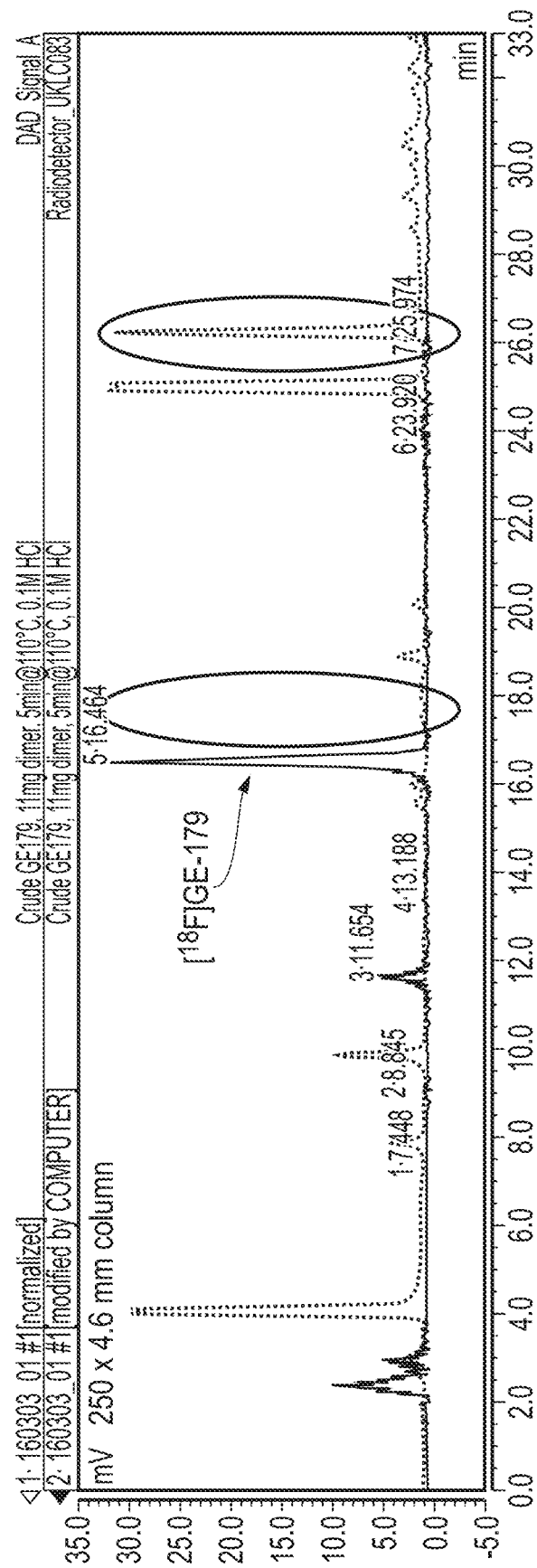

Mobile Phase A: 0.8% Triethylamine (TEA) [TEA (8 mL) and purified water (990 mL)]. Adjust the pH to around 7-7.5 with 85% H₃PO₄ (around 2.2 mL) and measure the pH using a calibrated pH meter FIG. 2 is a HPLC trace from reaction crude of [¹⁸F]GE-179 before and after optimization. The first trace is the crude before optimization and the second is after. It can be seen that the level of impurities decreased remarkably.

Example 4: Solid Phase Extraction Purification

A solid phase extraction method was developed to purify crude [¹⁸F]GE-179 on the FASTlab™ as follows:
Eluent A: 0.8% TEA [TEA (8 ml) and H₂O (900 ml)], pH adjusted to around 7 with 85% H₃PO₄ (around 2.4 ml). Water 10 (ml) was removed from Water (1000 μl) and added was TEA (8 ml) with pH adjusted to 7 with phosphoric acid.
FASTlab™ Wash Eluent (50 mL): Measured wash eluent (A) (30 mL) using a 50 mL measuring cylinder and poured into a 50 ml bottle. Measured acetonitrile (B) (20 mL) using a 50 mL measuring cylinder and poured into 50 ml bottle containing wash eluent and mixed.

1) Cassette loaded with 2 large environmental tC18 cartridges. Conditioned with ethanol (5 mL) followed with water (5 mL) on FASTlab™ during process.
2) Crude reaction was diluted with water (8 mL) and added to an external vial containing HCl (0.1 M, 4 mL). Loaded onto the 1st conditioned large tC18. (2 syringe loads)
3) First wash: $1^{st}$ SPE only, washed with FASTlab™ wash eluent (2×5 mL).
4) Second wash: $1^{st}$ and $2^{nd}$ SPE, washed with FASTlab™ wash eluent (3×5 mL).
5) Third wash: $2^{nd}$ SPE only, washed with water (2×7 mL).
6) Elution with acidified ethanol (Ethanol (50 ml) and HCl (4M) (300 μL): 1×2 mL
7) Formulation vol: 30 mL (10 mM PBS solution (28 ml) plus acidified ethanol (2 ml)).

The above wash eluent was made up of Eluent A (30 ml) and MeCN (20 ml) (40% MeCN: 60% Eluent A). Eluent A: 0.8% TEA (TEA (8 ml) and $H_2O$ (900 ml)), pH adjusted to around 7-7.5 with 85% $H_3PO_4$ (around 2.4 ml).

Figure 3:
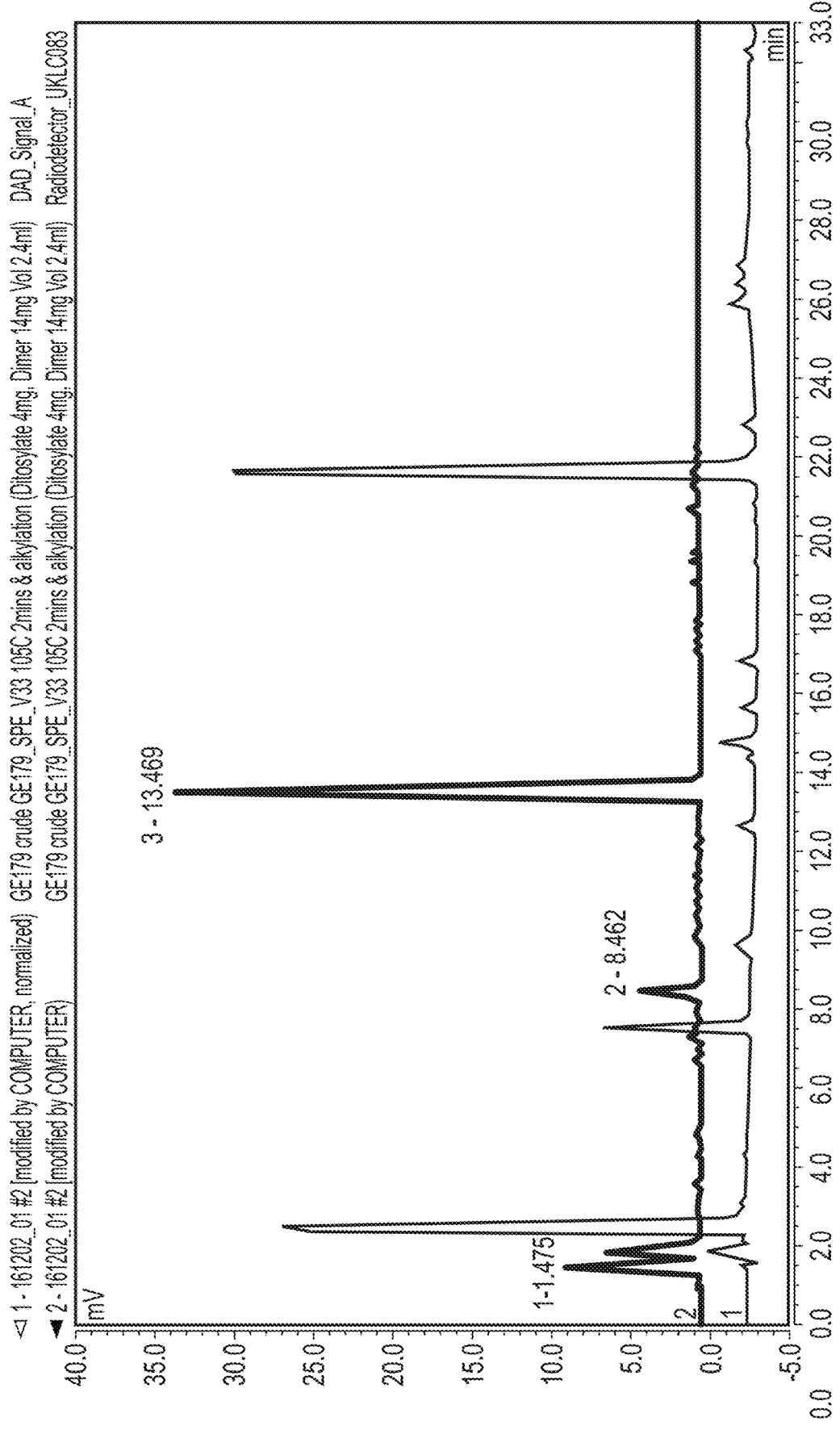
FIG. 3 is the HPLC trace before and after purification of crude [$^{18}$F]GE-179.
Figure 3:
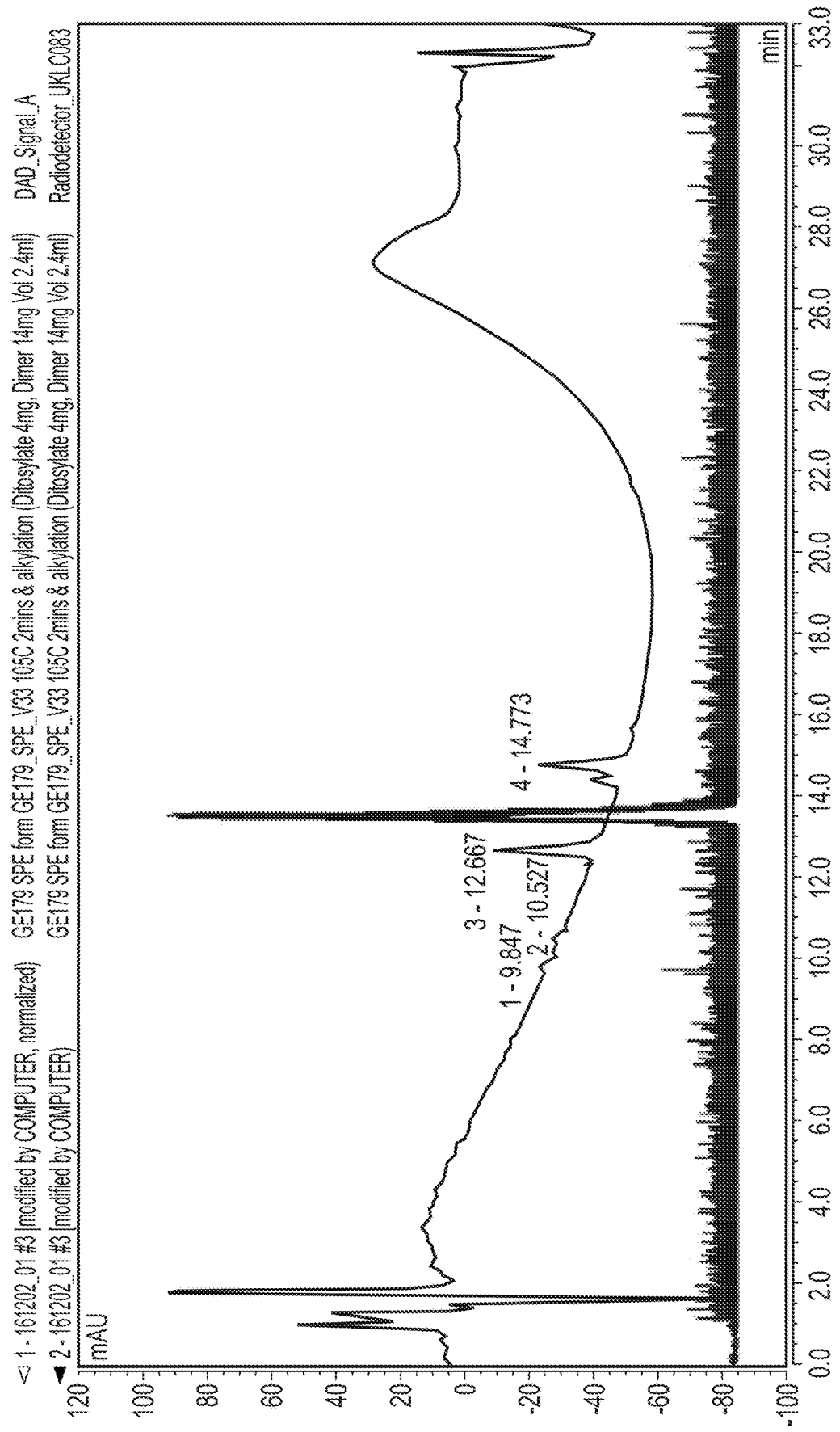

FIG. 3 shows the crude preparation before and after SPE purification.

The process was able to reduce the chemical content from a starting amount of around 10.000 μg of precursor to a total chemical content around 50 μg (1.7 μg/ml), whilst delivering a formulated isolated non decay corrected yield of 14-19%. The crude RCP was around 60% and the formulated RCP was >99%.

The invention claimed is:

1. A method to obtain a compound of Formula I:

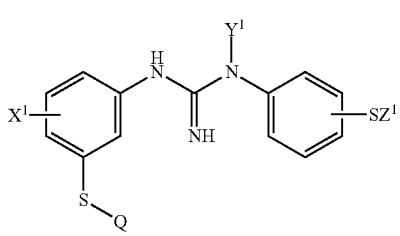

(I)

wherein:
$X^1$ is an X group selected from $C_{1-4}$ alkyl or halo;
$Y^1$ is a Y group selected from hydrogen or $C_{1-4}$ alkyl;
$Z^1$ is a Z group which is $C_{1-4}$ alkyl; and,
Q is $[^{11}C]C_{1-4}$ alkyl- or $[^{18}F]$—$C_{1-4}$fluoroalkyl-;
wherein said method comprises:
(i) reducing a compound of Formula II:

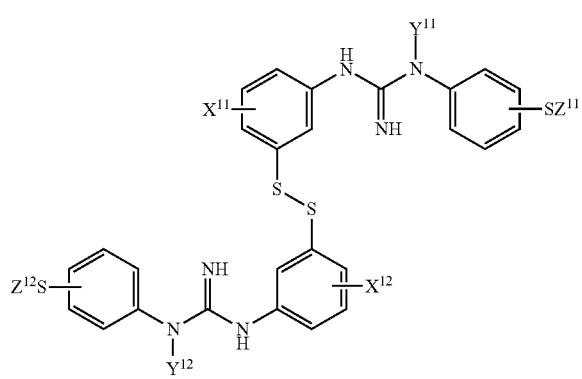

(II)

wherein:
(ii) $X^{11}$ and $X^{12}$ are the same and are both an X group as defined for $X^1$;
$Y^{11}$ and $Y^{12}$ are the same and are both a Y group as defined for $Y_1$; and,
$Z^{11}$ and $Z^{12}$ are the same and are both a Z group as defined for $Z^1$; and,
(ii) adding a base to the product of step (i) and reacting with either $[^{11}C]C_{1-4}$ alkyl-$LG^1$ or $[^{18}F]$—$C_{1-4}$ fluoroalkyl-$LG^2$, wherein $LG^1$ and $LG^2$ are independently halo, or the group —O—$SO_2$—$R^1$ wherein $R^1$ represents an optionally-substituted $C_{6-10}$ aryl, an optionally-substituted $C_{1-4}$ alkyl, or $C_{1-4}$ fluoroalkyl;
wherein the molar ratio of added base:thiol in step (ii) is in the range of about 0.2-0.75.

2. The method as defined in claim 1 wherein said compound of Formula II is a compound of Formula IIa:

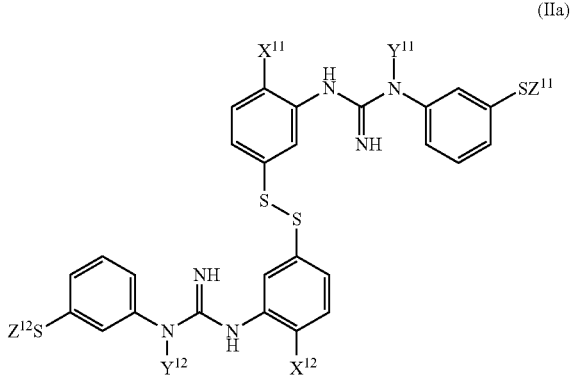

(IIa)

wherein:
$X_{11}$ and $X^{12}$ are the same and are both an X group as defined in claim 1;
$Y^{11}$ and $Y^{12}$ are the same and are both a Y group as defined in claim 1; and,
$Z^{11}$ and $Z^{12}$ are the same and are both a Z group as defined in claim 1.

3. The method as defined in claim 1 wherein said X group is halo.

4. The method as defined in claim 1 wherein said Y group is $C_{1-4}$ alkyl.

5. The method as defined in claim 1 wherein said Z group is methyl.

6. The method as defined in claim 1 wherein said X group is chloro, said Y group is methyl and said Z group is methyl.

7. The method as defined in claim 1 wherein reducing step (i) is effected using a reducing agent selected from sodium borohydride ($NaBH_4$), free phosphines, 1,8-Diazabicyclo [5.4.0]undec-7-ene (DBU), zinc in hydrochloric acid, zinc in acetic acid, magnesium in hydrochloric acid, sodium hydrogentelluride (NaTeH) in ethanol, lithium aluminium hydride ($LiAlH_4$) in tetrahydrofuran, indium in ammonium chloride, and sodium hydride (NaH), or a solid bound reducing agent such as triphenyl phosphone or phosphine.

8. The method as defined in claim 1 wherein reducing step (i) is effected using $NaBH_4$.

9. The method as defined in claim 1 wherein in said reacting step (ii) the thiol product is reacted with $[^{18}F]$—$C_{1-4}$ fluoroalkyl-$LG^2$.

10. The method as defined in claim 1 wherein said compound of Formula I is:

11. The method as defined in claim 1 wherein said compound of Formula II is:

[Chemical structure showing compound with Cl, NH, and ¹⁸F groups]

12. The method as defined in claim 1 wherein said reducing step (i) and said reacting step (ii) are carried out in the same vessel.

13. The method as defined in claim 1 wherein said reacting step is carried out in an ethanolic solution.

14. The method as defined in claim 1 wherein said reaction step (ii) is carried out for about 5-15 minutes.

15. The method as defined in claim 1 wherein said reaction step (ii) is carried out for about 5-10 minutes.

16. The method as defined in claim 1 wherein said reaction step (ii) is carried out for about 5 minutes.

17. The method as defined in claim 1 wherein said reacting step (ii) comprises about 0.02-0.04 mmol thiol.

18. The method as defined in claim 1 wherein said reacting step (ii) comprises about 0.02-0.035 mmol thiol.

19. The method as defined in claim 1 wherein said reacting step (ii) comprises about 0.03-0.035 mmol thiol.

20. The method as defined in claim 1 wherein said reacting step (ii) comprises about 0.005-0.025 mmol base.

21. The method as defined in claim 1 wherein said reacting step (ii) comprises about 0.01-0.025 mmol base.

22. The method as defined in claim 1 wherein said reacting step (ii) comprises about 0.02-0.025 mmol base.

23. The method as defined in claim 1 wherein said reacting step (ii) is carried out at a temperature between about 80-120° C.

24. The method as defined in claim 1 wherein said reacting step (ii) is carried out at a temperature between about 100-120° C.

25. The method as defined in claim 1 wherein said reacting step (ii) is carried out at a temperature between about 105-110° C.

26. The method as defined in claim 1 wherein said reacting step (ii) is carried out at a temperature of about 110° C.

27. The method as defined in claim 1 wherein said compound of Formula I is:

[Chemical structure showing compound with Cl, NH, and ¹⁸F groups]

said compound of Formula II is:

[Chemical structure showing disulfide-linked dimer compound]

said ratio of base:thiol is about 0.2-0.75; and,
said reacting step (ii) is carried out for about 5 minutes at about 110° C.

28. The method as defined in claim 1 which further comprises step (iii) purifying the reaction mixture obtained in step (ii) using solid phase extraction (SPE).

29. The method as defined in claim 28 wherein said SPE is carried out using one or more reverse phase SPE cartridges.

30. The method as defined in claim 29 wherein said SPE is carried out using one or more environmental tC18 SPE cartridges.

31. The method as defined in claim 30 wherein said SPE is carried out using two tC18 SPE cartridges.

32. The method as defined in claim 31 wherein chemical impurities are removed from said tC18 SPE cartridges using a basic aqueous acetonitrile solution and said purified compound of Formula I is eluted from said tC18 SPE cartridges with an ethanol solution.

33. The method as defined in claim 32 wherein said ethanol solution is an acidified ethanol solution.

34. The method as defined in claim 1 wherein said method is automated.

* * * * *